United States Patent [19]

Bomba et al.

[11] Patent Number: 5,371,232
[45] Date of Patent: Dec. 6, 1994

[54] PREPARATION OF 2-(4-AMINOPHENYL)BENZOTHIAZOLE COMPOUNDS

[75] Inventors: Christoph Bomba, Mannheim; Guido Kuth, Ludwigshafen; Paul Guenthert, Schifferstadt; Erwin Hahn, Heidelberg, all of Germany

[73] Assignee: BASF Aktiengesellschaft, Ludwigshafen, Germany

[21] Appl. No.: 99,554

[22] Filed: Jul. 30, 1993

[30] Foreign Application Priority Data

Aug. 14, 1992 [DE] Germany .............. 4227029

[51] Int. Cl.$^5$ ............................................. C07D 277/82
[52] U.S. Cl. ........................................... 548/152; 548/178
[58] Field of Search ............................................. 548/152

[56] References Cited

U.S. PATENT DOCUMENTS

| | | |
|---|---|---|
| 2,795,614 | 6/1957 | De Garmo et al. . |
| 3,462,448 | 8/1969 | Kelyman .............. 548/152 |
| 3,772,309 | 11/1973 | Marvel et al. . |
| 3,832,320 | 8/1974 | Aponyi et al. ............ 548/152 |
| 4,064,136 | 12/1977 | Loew et al. ............. 548/152 |

FOREIGN PATENT DOCUMENTS

| | | |
|---|---|---|
| 2106200 | 9/1972 | Germany . |
| 2333378 | 1/1975 | Germany . |

OTHER PUBLICATIONS

Chemical Abstracts, vol. 105, No. 21, Nov. 24, 1986, An 191069y, Karel Pastalka, et al., "2-(4-Aminophenyl-)-6-Methylbenzothiazole".
Ullmans Enzyklopadie der Technischen Chemie 3 Auft., Bdg. 17 (1866) pp. 333-336.

(List continued on next page.)

*Primary Examiner*—Joseph Paul Brust
*Assistant Examiner*—Mary Susan H. Gabilan
*Attorney, Agent, or Firm*—Oblon, Spivak, McClelland, Maier & Neustadt

[57] ABSTRACT

A process for preparing a compound of the formula I

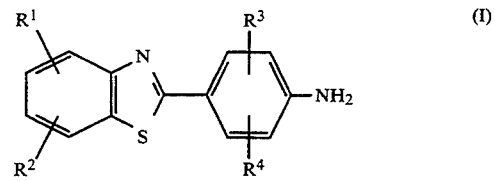

where $R^1$ to $R^4$ are each, independently of one another, hydrogen, alkyl, alkoxy, hydroxyl or halogen, comprises reacting a compound of the formula II

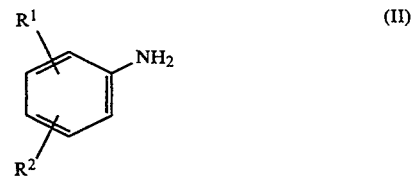

with a compound of the formula III

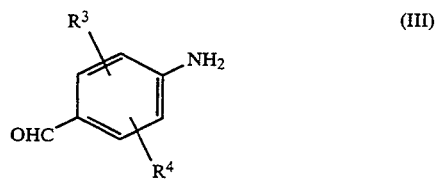

in the presence of sulfur or a sulfur donor at elevated temperature.

The compounds prepared according to the invention are suitable, for example, as diazo components.

6 Claims, No Drawings

OTHER PUBLICATIONS

A. I. Kirprianov and V. A. Schrubovich Steric Hindrance in Molecules of 2-Arylbenzithiazoles (1960) pp. 3710–3713.

T. G. Deligeorgiev Dyes and Pigments 12 (1990) pp. 243–248.

H. Lankelma and P. F. Sharnoff F. Am. Chem. Soc., vol. 54 (1932) pp. 379–381.

H. Lankelma and P. F. Sharnoff F. Am. Chem. Soc., vol. 53 (1931) pp. 2654–2657.

H. T. Bogert and A. Still F. Am. Chem. Soc., vol. 47 (1925) pp. 3078–3083.

Katritzky et al., Comprehensive Heterocyclic Chemistry vol. 6 (1984), pp. 321–386.

Katritzky et al., Energy & Fuels (1990), 4, pp. 547–555.

Perregaard et al., Acta Chemica Scandinavica B, 31 (1977), pp. 203–208.

PREPARATION OF 2-(4-AMINOPHENYL)BENZOTHIAZOLE COMPOUNDS

It is known that substituted 2-(4-aminophenyl)-benzothiazoles can be prepared by condensing o-aminothiophenols with aromatic amines in the presence of an oxidizing agent either with the use of a solvent [e.g. A. W. Hoffmann, Ber., 13 (1880) 1236; M. T. Bogert and A. Stull, J. Am. Chem. Soc., 47 (1925) 3078; H. Lankelma and P. J. Sharnoff, J. Am. Chem. Soc., 53 (1931) 2654 and 54 (1932) 379; Research Corp., U.S. Patent 3,772,309 (1973); BASF AG Offenlegungsschrift 2,333,378 (1975) or T. G. Deligeorgiev, Dyes and Pigments 12 (1990) 243] or without solvent [e.g. A. I. Kiprianov and V. A. Shrubovich, Zh. Obshch. Kihm., 30 (1960) 3746].

Ullmanns Encyklopädie der technischen Chemie, 3rd edition, Vol. 17 (1966), pages 333-334, discloses the preparation of dehydrothiotoluidine in which a mixture of p-toluidine, sulfur and sodium carbonate is heated initially at 180° C. and subsequently at up to 222° C. The yield of purified dehydrothiotoluidine is 57% of theory.

The present invention now relates to the process indicated in the claims, in which amines of the formula II are reacted with sulfur and compounds of the formula III.

Substituents $R^1$ to $R^4$ which may be mentioned are, besides those already specified, fluorine, chlorine or bromine and $C_1$-$C_6$-alkyl or -alkoxy such as methyl, ethyl, n- or i-propyl, n-, i- or tert-butyl, hexyl, methoxy, ethoxy or butoxy. $R^1$ is preferably methyl, and $R^2$ to $R^4$ are preferably each hydrogen.

The process according to the invention is expediently carried out by gradually introducing the compound of the formula III into a liquid mixture of the compound of the formula II and sulfur.

The reaction is, as a rule, carried out at from 150 to 230, preferably from 170° to 190,°C. It is more-over advantageous to use the compound of the formula III in the form of an azomethine, and preferred amine components are compounds of the formula II.

It is particularly preferred in the process according to the invention for the ratio of the compounds of the formula III and II to be from 0.6 to 1.0, and the compound of the formula III can also be wholly or partly in the form of an azomethine.

Compounds of the formula III can be prepared by, for example, the process described in U.S. Pat. 2,795,614.

The process according to the invention provides the compounds of the formula I in excellent yield and purity after removal of the excess of the compound of the formula II. The compounds of the formula II are normally used in a 2-12-fold, preferably 4-8-fold, molar excess based on the compounds of the formula III. Sulfur is expediently used in a 1.5-3.5-fold, preferably 2.25-2.75-fold, excess.

After the reaction is complete, the compounds of the formula II can be removed by distillation. The compounds of the formula I can be purified by, for example, recrystallization or solid distillation, but it is also possible, because of their high purity, to use them directly for further reactions, for example sulfation or diazotization.

Compounds of the formula I with or without sulfo group are valuable diazo components.

Details of the process according to the invention are evident from the Examples in which, unless otherwise indicated, parts and percentages are by weight.

EXAMPLE 1

43 parts of a p-aminobenzaldehyde/p-toluidine mixture (molar ratio about 0.65) are added, continuously or in portions, over a period of 6 hours to a melt of 100 parts of p-toluidine and 12 parts of sulfur at an internal temperature of 175°-180° C. After the reaction is complete, the excess p-toluidine is removed by distillation. The crude melt (about 47 parts) contains approximately 95% 2-(4-aminophenyl)-6-methylbenzothiazole (dehydrothiotoluidine). It can be sulfated and/or diazotized without further purification and then converted into valuable paper dyes.

EXAMPLE 2

24 parts of p-aminobenzaldehyde are added to a melt of 100 parts of aniline and 14 parts of sulfur in a similar manner to Example 1. The crude melt obtained after removal of the aniline contains approximately 80% 2-(4-aminophenyl)benzothiazole.

EXAMPLE 3

17 parts of p-aminobenzaldehyde are added to a melt of 100 parts of p-anisidine and 11 parts of sulfur in a similar manner to Example 1. The crude melt obtained after removal of the p-anisidine contains approximately 80% 2-(4-aminophenyl)-6-methoxybenzothiazole.

We claim:

1. A process for preparing a compound of the formula I

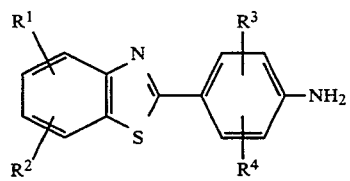

wherein $R^1$ to $R^4$ are each, independently of one another, hydrogen, alkyl, alkoxy, hydroxyl, or halogen, which comprises reacting a compound of the formula II

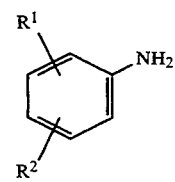

and sulfur or a sulfur donor with a compound of the formula III

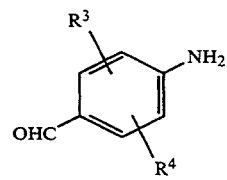

wherein the yield of said compound of the formula I is from 80–95%.

2. A process as claimed in claim 1, wherein the reaction is carried out with an excess of compound II.

3. A process as claimed in claim 1, wherein the compound of the formula III is gradually added to a mixture of the compound of the formula II and sulfur.

4. A process as claimed in claim 1, wherein the compound of the formula III is used in the form of an azomethine.

5. The process as claimed in claim 1, which consists of reacting a compound of formula

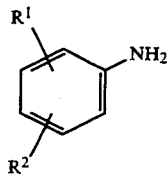 (II)

and sulfur or a sulfur donor with a compound of a formula III

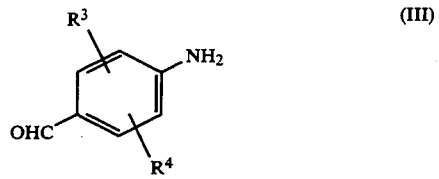 (III)

wherein the yield of said compound of the formula I is from 80–95%.

6. The process as claimed in claim 1, wherein $R^1$ is methyl and $R^{2-4}$ are each hydrogen.

* * * * *